United States Patent
Nakajima et al.

(10) Patent No.: US 8,138,473 B2
(45) Date of Patent: *Mar. 20, 2012

(54) MASS SPECTROMETRY UNIT

(75) Inventors: Toyoaki Nakajima, Chigasaki (JP); Yujirou Kurokawa, Chigasaki (JP); Tsutomu Yuri, Chigasaki (JP); Ryota Tanaka, Chigasaki (JP); Shuji Yoshida, Chigasaki (JP)

(73) Assignee: Ulvac, Inc., Chigasaki-Shi (JP)

( * ) Notice: Subject to any disclaimer, the term of this patent is extended or adjusted under 35 U.S.C. 154(b) by 44 days.

This patent is subject to a terminal disclaimer.

(21) Appl. No.: 12/599,301

(22) PCT Filed: Apr. 14, 2008

(86) PCT No.: PCT/JP2008/057249
§ 371 (c)(1),
(2), (4) Date: Nov. 9, 2009

(87) PCT Pub. No.: WO2008/139809
PCT Pub. Date: Nov. 20, 2008

(65) Prior Publication Data
US 2010/0213363 A1    Aug. 26, 2010

(30) Foreign Application Priority Data
May 15, 2007    (JP) .................... P2007-129408

(51) Int. Cl.
*H01J 49/26*    (2006.01)
*B01D 59/44*    (2006.01)

(52) U.S. Cl. ........ 250/288; 250/281; 250/282; 250/287; 250/423 R; 250/424

(58) Field of Classification Search .................. 250/288, 250/281, 282, 287, 423 R, 424
See application file for complete search history.

(56) References Cited

U.S. PATENT DOCUMENTS

| | | |
|---|---|---|
| 3,274,436 A | 9/1966 | Reich |
| 5,561,292 A | 10/1996 | Buckley et al. |
| 5,907,154 A | 5/1999 | Shimomura |

(Continued)

FOREIGN PATENT DOCUMENTS

DE    1498845    5/1969

(Continued)

OTHER PUBLICATIONS

International Search Report dated Jun. 17, 2008 issued in related International Patent Application No. PCT/JP2008/057249.

(Continued)

*Primary Examiner* — Nikita Wells
(74) *Attorney, Agent, or Firm* — Grossman, Tucker, Perreault & Pfleger, PLLC

(57) ABSTRACT

A mass spectrometry unit of the present invention includes a mass spectrometry portion that detects ion current values of a gas to be measured according to mass-to-charge ratio, to thereby measure partial pressures of the gas to be measured. The mass spectrometry unit further includes: a control portion for preliminary storing a record of a mass-to-charge ratio of a specific gas that decreases a function of a specific portion of the mass spectrometry unit, in which if an ion current value with the mass-to-charge ratio of the specific gas detected by the mass spectrometry portion is not less than a predetermined value, the control portion outputs a warning signal denoting a functional decrease in the specific portion.

5 Claims, 9 Drawing Sheets

U.S. PATENT DOCUMENTS

| | | |
|---|---|---|
| 6,259,210 B1 | 7/2001 | Wells |
| 6,806,450 B2 | 10/2004 | Nakashige et al. |
| 7,355,171 B2 * | 4/2008 | Ludviksson .................. 250/288 |
| 2001/0042836 A1 | 11/2001 | Olson et al. |
| 2008/0156980 A1 * | 7/2008 | Rather et al. .................. 250/287 |
| 2009/0090854 A1 | 4/2009 | Nakajima et al. |
| 2010/0133429 A1 * | 6/2010 | Nakajima et al. ............. 250/282 |

FOREIGN PATENT DOCUMENTS

| | | |
|---|---|---|
| JP | 49-127687 | 12/1974 |
| JP | 1-281651 | 11/1989 |
| JP | 3-261061 | 11/1991 |
| JP | 3-283252 | 12/1991 |
| JP | 1154083 | 2/1992 |
| JP | 485565 | 7/1992 |
| JP | 05109860 | 4/1993 |
| JP | 05275052 | 10/1993 |
| JP | 07151816 | 6/1995 |
| JP | 8-306333 | 11/1996 |
| JP | 08321277 | 12/1996 |
| JP | 09022681 | 1/1997 |
| JP | 09171083 | 6/1997 |
| JP | 09324269 | 12/1997 |
| JP | 10213508 | 8/1998 |
| JP | 1154083 | 2/1999 |
| JP | 2000-036283 | 2/2000 |
| JP | 2000-132284 | 5/2000 |
| JP | 2000-223064 | 8/2000 |
| JP | 2000-314723 | 11/2000 |
| JP | 2001-15060 | 1/2001 |
| JP | 2002-033075 | 1/2002 |
| JP | 2002042721 | 2/2002 |
| JP | 2003329647 | 11/2003 |
| JP | 200428675 | 1/2004 |
| JP | 2004177213 | 6/2004 |
| JP | 2004349102 | 12/2004 |
| JP | 2006267129 | 10/2006 |
| JP | 2006-329662 | 12/2006 |
| JP | 2006-352963 | 12/2006 |

OTHER PUBLICATIONS

International Search Report issued in related International Patent Application No. PCT/JP2008/057248 dated Jun. 10, 2008.

Office Action from related Korean Application No. 10-2009-7024728 dated Aug. 5, 2011. English translation attached.

Office Action from corresponding German Application No. 11 2008 001 001.3 dated Jul. 20, 2011. English translation attached.

Office Action from corresponding Japanese Application No. 2009-514039 dated Oct. 18, 2011. English translation attached.

Office Action from corresponding Japanese Application No. 2009-511789 dated Oct. 18, 2011. English translation attached.

* cited by examiner

FIG. 8

SERIAL NUMBER OF ANALYSIS TUBE    000327

SERIAL NUMBER OF PUMP    000930

| MASS-TO-CHARGE RATIO (m/z) | GAS SPECIES | INTEGRATED VALUE OF ION CURRENT |
|---|---|---|
| 20 | HF | $1e-3 A \cdot s$ |
| 35 | Cl | — |
| 70 | $Cl_2$ | — |
| 71 | $NF_3$ | — |
| 81 | HBr | — |
| 88 | $CF_4$ | — |
| 100 | $SiH_2Cl_2$ | — |
| 139 | $C_2F_6$ | — |

MASS SPECTROMETRY UNIT

TECHNICAL FIELD

The present invention relates to a mass spectrometry unit. Priority is claimed on Japanese Patent Application No. 2007-129408, the contents of which are incorporated herein by reference.

BACKGROUND ART

In a manufacturing process of semiconductor apparatuses and flat panel displays (FPDs), a variety of vacuum apparatuses are utilized. To perform a process management of the vacuum apparatuses, quadrupole mass analyzers are used. The mass analyzers are apparatuses for measuring partial pressures of a variety of substances included in the gas to be analyzed according to their mass-to-charge ratio (mass number/charge number). In addition, in recent years, the mass analyzers are used in a wide variety of fields such as an assaying of materials, an analysis of biopolymer compounds such as protein, and security. Therefore, there is an increasing demand for mass analyzers.

A quadrupole mass analyzer energizes a filament as an ion source portion in a mass spectrometer tube to cause thermions to be emitted, to thereby ionize a gas and generate ions. In an ion detector for detecting ionized ions, a secondary electron multiplier tube made of a Cu—Be alloy, an aluminum oxide (AlO), and the like is often utilized.

However, faulty observance of instructions and directions for use of mass analyzers leads to a failure in a filament or an ion detector. Furthermore, each filament and ion detector has an operating life. If the operating life is exceeded, it is not possible to obtain correct measurement. Therefore, to prevent a failure in, to identify the operating life of, and to extend the operating life of a filament and an ion detector, for example configurations as follows are disclosed.

A filament is capable of glowing only when the pressure is not greater than approximately 1 Pa. At pressures more than that, there is a possibility that the filament will be broken. Therefore, in Patent Document 1, to prevent a failure in a filament and an ion detector, a pressure detection portion of a vacuum gage is placed in a mass analyzer, to thereby prevent a break in a filament. In Patent Document 2, an overcurrent prevention circuit for a filament is added, to thereby prevent a break in a filament. In Patent Document 3, a filament current is detected to estimate the operating life of a filament.

On the other hand, in Patent Document 4, detection of unnecessary ions is avoided to extend the operating life of an ion detector. In Patent Document 5, a gas flow rate of a calibration gas is determined on a mass spectrum pattern for optimization of the flow rate, to thereby prevent a deterioration in sensitivity of an ion detector and to thereby detect contamination in an ion source portion. In Patent Document 6, materials and configurations used for an ion detector are selected, to thereby extend the operating life of the ion detector.

Furthermore, a mass analyzer is capable of being operated only at pressures not more than the use pressure as described above. Therefore, if the pressure is high, a pumping system called a differential pumping system may be used, which is added to the mass analyzer to construct a mass spectrometry unit. In this case, a failure in the pumping system may lead to a failure in the mass analyzer. To prevent this, for example in Patent Document 7, each of a preventive maintenance solution before the occurrence of an anomaly of a pump, a solution to a fault at the occurrence to the anomaly, and a risk aversion solution after the occurrence of the anomaly according to the states before and after the anomaly, is displayed, output as an electric signal or as speech, to thereby perform a preventive maintenance.

Patent Document 1: Japanese Unexamined Patent Application, First Publication No. 2004-349102
Patent Document 2: Japanese Patent No. 3734913
Patent Document 3: Japanese Unexamined Patent Application, First Publication No. H07-151816
Patent Document 4: Japanese Unexamined Patent Application, First Publication No. H09-22681
Patent Document 5: Japanese Unexamined Patent Application, First Publication No. H08-321277
Patent Document 6: Japanese Unexamined Patent Application, First Publication No. H09-171083.
Patent Document 7: Japanese Unexamined Patent Application, First Publication No. 2004-177213
Patent Document 8: Japanese Unexamined Patent Application, First Publication No. H05-275052
Patent Document 9: Japanese Unexamined Patent Application, First Publication No. H05-109860

In a manufacturing process of semiconductor apparatuses, FPDs, and the like, an etching apparatus, a chemical vapor deposition (CVD) apparatus, or the like is used. When a mass spectrometry unit is used in such apparatuses, a corrosive/halogen-based gas introduced into the etching apparatus or a gas filled in the CVD apparatus for depositing a metal/insulating film has an adverse influence on a filament or an ion detector. For example, if a filament is exposed to a corrosive-halogen-based gas, a coating made of yttrium oxide on the surface of the filament comes off, finally bringing about a possibility of the occurrence of an anomaly such as a break in the filament and the stopping of an emission current flowing between the filament and the grid. Furthermore, a secondary electron multiplier tube as an ion detection portion is for generating secondary electrons by causing ions to collide with its metal surface at a high speed. Therefore, if a metal/insulating film is deposited on the metal surface, there is a possibility that secondary electrons are less likely to be generated. Therefore, in Patent Documents 8 and 9, there is proposed a technique that enables reactive gas monitoring even during a deposition operation. Note that a gas that decreases the function of a specific portion in a mass spectrometry unit such as a corrosive/halogen-based gas or a gas for depositing a metal/insulating film will be hereinafter referred to as a "specific gas."

While the operating life and performance of mass spectrometry units have improved and their demand has grown, there are increasing number of users who use mass spectrometry units without regard to instructions and directions for use. To be more specific, different mass spectrometry units should be used according to their applications such as the gases and apparatuses that they are to measure. However, sometimes, they are used without regard to the applications. Therefore, it sometimes happens that an unexpected specific gas is introduced into a mass spectrometry unit. As a result, filaments, ion detectors, and the like often suffer from a failure before they reach the end of their operating life.

As described above, a filament, an ion detector, and the like are parts with an operating life, and hence, require regular replacement. However, the time for their replacement is subject to change according to the condition of use and the circumstances of use. Therefore, it is difficult to determine the correct time for their replacement. If the filament, the ion detector, or the like is replaced after it is unusable and a correct measurement is impossible, there arises a problem of an extended period in which use of the mass spectrometry unit is suspended. In addition, if the filament, the ion detector, or the like is replaced in advance although it is still usable, there arises a problem of a loss of resources and costs.

Furthermore, when the filament, the ion detector, or the like is replaced, or when the pump is overhauled, there is a possibility that a specific gas is deposited on the filament, the ion detector, or the like. Therefore, it is required to secure the safety of the worker. Conventionally, the worker starts working after asking the user about the introduction history of a specific gas each time the replacement or the overhaul is done. This has resulted in extra time in replacement work.

In the case where the mass spectrometry unit is used for an etching/CVD apparatus, the mass spectrometry portion and the pump used in the differential exhaustion system are heated even during measurement, to thereby prevent deposition of metal/insulating matter. Through the pump, a purge gas (for example, $N_2$) is introduced to dilute a corrosive-halogen-based gas. After completion of the measurement, it is not necessary to heat the mass spectrometry tube and the pump and to purge the pump if the aforementioned corrosive/halogen-based gas, the aforementioned gas for depositing a metal/insulating film, or the like is not introduced therein. Nevertheless, if the heating of the mass spectrometry tube and the pump, and the purge of the pump are continued in operation, there arises a problem in that electric power and gas are wasted.

DISCLOSURE OF INVENTION

The present invention has been achieved to solve the above problems, and has an object to provide a mass spectrometry unit capable of preventing a functional decrease in a specific portion and capable of correctly grasping a deterioration time of the specific portion.

The present invention has another object to provide a mass spectrometry unit capable of efficiently performing repair work and the like on a part to be repaired and hence, capable of saving electric power.

To solve the above problems, the present invention adopts the followings.

(1) A mass spectrometry unit of the present invention includes a mass spectrometry portion that detects ion current values of a gas to be measured according to mass-to-charge ratio, to thereby measure partial pressures of the gas to be measured. The mass spectrometry further includes: a control portion for preliminary storing a record of mass-to-charge ratios of specific gases that decrease a function of a specific portion of the mass spectrometry unit, in which if an ion current value with the mass-to-charge ratio of any of the specific gases detected by the mass spectrometry portion is not less than a corresponding predetermined value, the control portion outputs a warning signal denoting a functional decrease in the specific portion.

With this configuration, mass-to-charge ratios of the specific gases that decrease the function of the specific portion in the mass spectrometry unit are recorded in the control portion. If an ion current value of any of the specific gas exceeds the corresponding predetermined value, then a warning signal denoting a functional decrease in the specific portion is output. Thereby, even if an unexpected specific gas is introduced or even if the user is not aware of the mass-to-charge ratios of the specific gases, it is possible to promptly notify the possibility of a functional decrease in the specific portion of the mass spectrometry unit. Therefore, it is possible to prevent a functional decrease in the specific portion due to the specific gas.

(2) Another mass spectrometry unit of the present invention includes a mass spectrometry portion that detects ion current values of a gas to be measured according to mass-to-charge ratio, to thereby measure partial pressures of the gas to be measured. The mass spectrometry further includes: a control portion for preliminary storing a record of mass-to-charge ratios of specific gases that decrease a function of a specific portion of the mass spectrometry unit, in which if an integrated value of an ion current value of any of the specific gases detected by the mass spectrometry portion over a detection time during which the ion current value is being detected is not less than a corresponding predetermined value, the control portion outputs a warning signal denoting a functional decrease in the specific portion, and also cancels an application of a voltage to the specific portion, to thereby stop a function of the specific portion.

With this configuration, an output of a warning signal denoting a functional decrease in the specific portion makes it possible to correctly notify a change over time of the specific portion corresponding to the integrated value of the ion current value of any of the specific gas over its detection time. Furthermore, the application of the voltage to the specific portion is cancelled to stop the function of the specific portion. Thereby, it is possible to suppress a further change over time of the specific portion.

(3) In the mass spectrometry unit according to the above (2), the predetermined value may be not greater than an integrated value of the ion current value until a deterioration of the specific portion over the detection time.

In this case, it is possible to correctly inform the operating life of the specific portion in the mass spectrometry unit. Accordingly, the user can determine the replacement time of the specific portion. Therefore, it is possible to prevent the replacement of the specific portions after the specific portion is unusable or the advance replacement while it is still usable. As a result, the specific portion can be used to a maximum extent. Therefore, it is possible to suppress costs, and also to achieve resource saving.

(4) Another mass spectrometry unit of the present invention includes a mass spectrometry portion that detects ion current values of a gas to be measured according to mass-to-charge ratio, to thereby measure partial pressures of the gas to be measured. The mass spectrometry further includes: a control portion for preliminary storing a record of mass-to-charge ratios of specific gases, the gases are checked for a presence or absence of a deposition thereof onto a part to be repaired at repair work of the mass spectrometry unit, in which if an ion current value with the mass-to-charge ratio of any of the specific gases is detected by the mass spectrometry portion, the control portion records at least one of information on the specific gas and information on the part to be repaired.

With this configuration, if an ion current value with the mass-to-charge ratio of any of the specific gases is detected by the mass spectrometry portion, then information on the specific gas and/or information on the part to be repaired are recorded. This makes it possible to check whether a deposition of the specific gas on the part to be repaired is present or not correctly and speedily. Therefore, even when a worker other than the user performs repair work of the part to be repaired, the worker is allowed to do their work with efficiency and with their safety secured.

(5) Another mass spectrometry unit of the present invention is a mass spectrometry unit including a mass spectrometry portion that detects ion current values of a gas to be measured according to mass-to-charge ratio, to thereby measure partial pressures of the gas to be measured, further including: a control portion for previously storing a record of mass-to-charge ratios of specific gases that decrease a function of a specific portion of the mass spectrometry unit; and a specific portion maintenance device for preventing a functional decrease in the specific portion due to any of the specific gases, in which if an ion current value with the mass-to-charge ratio of any of the specific gases detected by the mass spectrometry portion is not greater than a predetermined value, the control portion stops the specific portion maintenance device.

With this configuration, if no specific gas that decreases the function of the specific portion in the mass spectrometry unit is introduced, then the specific portion maintenance device is stopped. Thereby, it is possible to achieve power saving of the mass spectrometry unit.

According to the mass spectrometry unit of the present invention, mass-to-charge ratios of the specific gases that decrease the function of the specific portion in the mass spectrometry unit are recorded in the control portion. If an ion current value of any of the specific gas exceeds the corresponding predetermined value, then a warning signal denoting a functional decrease in the specific portion is output. Thereby, even if an unexpected specific gas is introduced or even if the user is not aware of the mass-to-charge ratios of the specific gases, it is possible to promptly notify the possibility of a functional decrease in the specific portion of the mass spectrometry unit. Therefore, it is possible to prevent a functional decrease in the specific portion due to the specific gas. Consequently, it is possible to efficiently use the mass spectrometry unit for a long period of time.

Furthermore, if an ion current value with the mass-to-charge ratio of any of the specific gas is detected by the mass spectrometry portion, then information on the specific gas and/or information on the part to be repaired are recorded. This makes it possible to check correctly and speedily whether a deposition of the specific gas on the part to be repaired is present or not. Therefore, even when a worker other than the user performs repair work of the part to be repaired, the worker is allowed to do their work with efficiency and with their safety secured.

Furthermore, if no specific gas that decreases the function of the specific portion in the mass spectrometry unit is introduced, then the specific portion maintenance device is stopped. Thereby, it is possible to achieve power saving of the mass spectrometry unit.

BRIEF DESCRIPTION OF THE DRAWINGS

FIG. 8 is an exemplary record of specific gases and serial numbers of a measurement portion and a pump in a parts management method of the mass spectrometry unit according to the embodiment.

DESCRIPTION OF THE REFERENCE SYMBOLS

Figure 1:
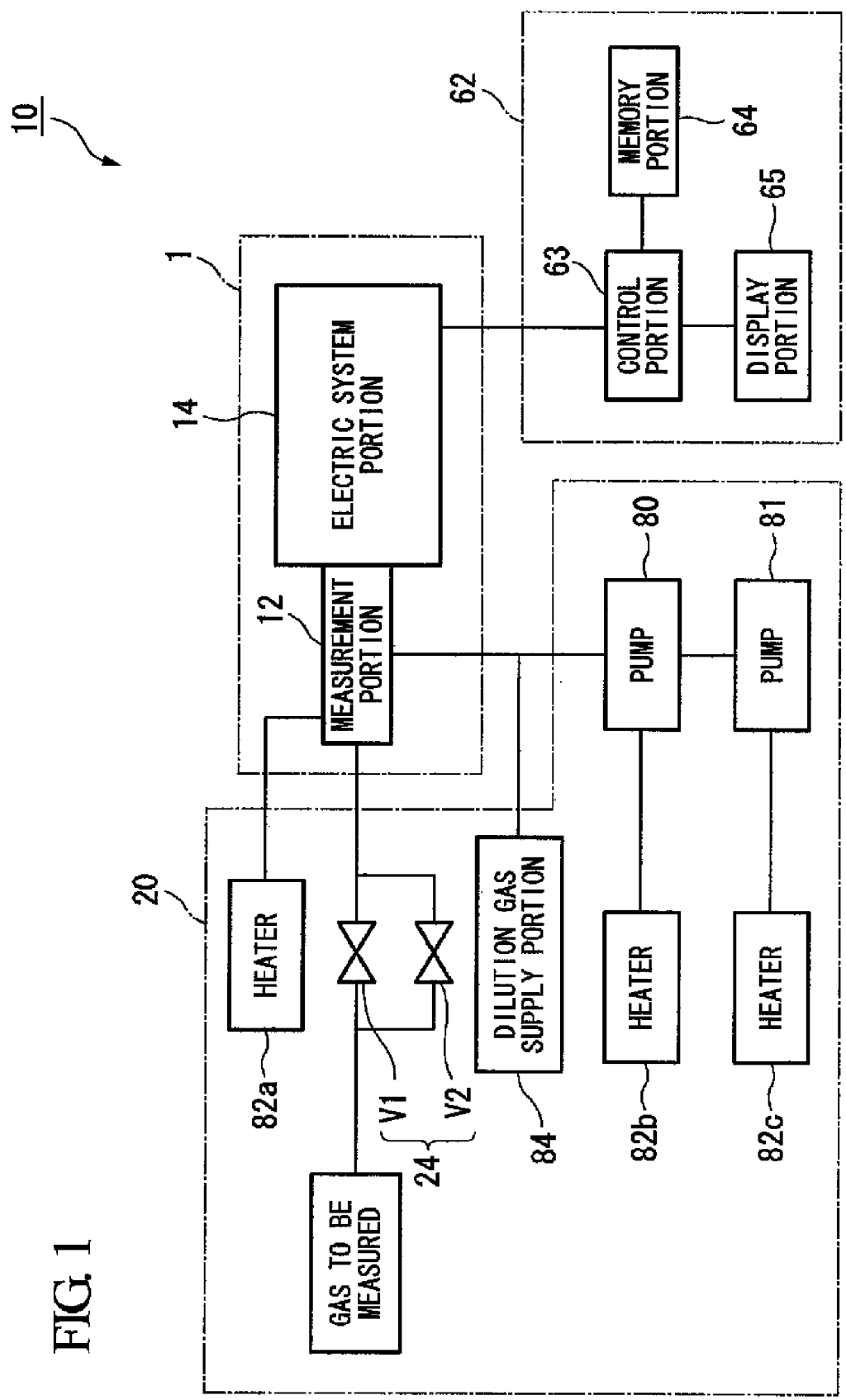
FIG. 1 is a block diagram showing a mass spectrometry unit according to one embodiment of the present invention.

1: mass spectrometry portion
10: mass spectrometry unit
22: ion source portion (specific portion, part to be repaired)
27: ion detection portion (specific portion, part to be repaired)
63: control portion
80: turbomolecular pump (part to be repaired)
81: fore pump (part to be repaired)
82: baking heater (specific portion maintenance device)
84: dilution gas supply portion (specific portion maintenance device)

BEST MODE FOR CARRYING OUT THE INVENTION

Hereunder is a description of one embodiment of the present invention with reference to the drawings. In the drawings used in the following description, scales of the respective members are optionally modified to make their size recognizable.

(Mass Spectrometry Unit)

FIG. 1 is a block diagram showing a mass spectrometry unit according to the present embodiment.

Mass analyzers include a magnetic sector type, a quadrupole type, and other types. In the present embodiment, a transducer-type quadrupole mass analyzer will be described by way of example. The quadrupole mass analyzer identifies the types of gases present in the gas to be measured, and the partial pressures of the gases.

A mass spectrometry unit 10 according to the present embodiment includes: a mass spectrometry portion 1; a differential exhaustion portion 20 for reducing the pressure of a gas to be measured that is introduced into the mass spectrometry portion 1 to a predetermined value; and a controlling PC (a control portion) 62 for controlling the mass spectrometry portion 1 and the differential exhaustion portion 20. The mass spectrometry portion 1 includes: a measurement portion 12 for measuring partial pressures of the gas to be measured according to the mass-to-charge ratio; and an electric system portion 14 provided continuously to the measurement portion 12 for driving the measurement portion 12 based on a signal that is output from the controlling PC 62.

The differential exhaustion portion 20 includes: a gas introduction portion 24 for introducing the gas to be measured into the measurement portion 12; a turbomolecular pump 80 (a part to be repaired) for reducing a pressure of a part of the gas to be measured that is introduced into the measurement portion 12; and a fore pump (a part to be repaired: for example, a diaphragm pump) 81 connected to the turbomolecular pump 80 (hereinafter, both pumps together will be referred to as the pumps 80, 81).

The gas introduction portion 24 includes selector valves V1, V2 for enabling selection of the amounts of the gas to be measured. With the selector valve V2, an orifice is combined, making it possible to reduce an amount of the gas introduced into the measurement portion 12 to a small amount compared with the case of the selector valve V1. That is, to make the amount of the gas introduced into the measurement portion 12 is small, the selector valve V2 is selected.

The differential exhaustion portion 20 is driven when the pressure of the gas to be measured in the measurement portion 12 is not lower than the range that allows the measurement portion 12 to favorably operate (the range of not higher than $10^{-2}$ Pa), to thereby reduce the pressure in the measurement portion 12 to a predetermined pressure.

To the measurement portion 12, there is connected a baking heater 82a (a specific portion maintenance device). To the pump 80, there is connected a baking heater 82b (a specific portion maintenance device). To the pump 81, there is connected a baking heater 82c (a specific portion maintenance device). The baking heater 82a evaporates the moisture present in the measurement portion 12, and exhausts the vapor present in the measurement portion 12, to thereby reduce the pressure in the measurement portion 12. The baking heaters 82b, 82c heat the interiors of the pumps 80, 81, respectively, to thereby prevent a metal/insulating film produced from the gas to be measured from depositing on the interiors of the pumps 80, 81.

Furthermore, between the measurement portion 12 and the turbomolecular pump 80, there is connected a dilution gas supply portion 84 (a specific portion maintenance device) for diluting the gas to be measured that flows through the pumps 80, 81. In the present embodiment, for example nitrogen ($N_2$) or the like is used as the dilution gas (purge gas).

The controlling PC 62 includes: a control portion 63; a memory portion 64; and a display portion 65. The control portion 63 sends an output signal to the electric system portion 14 based on the mass-to-charge ratio detected by the measurement portion 12 and also based on its corresponding ion current value, to thereby control the operations of the mass spectrometry portion 1 and the differential exhaustion portion 20. In the memory portion 64, predetermined values (described later) and various pieces of data are recorded and stored. The display portion 65 is for making information of the measurement portion 12 visually recognizable to the user. The display portion 65 displays various pieces of information including the mass-to-charge ratio detected by the control portion 63, the size of ion current value corresponding to the mass-to-charge ratio, and a warning display (described later). The ion current value is proportional to the amount of incident ions. Therefore, the size of the ion current value reveals the amount of ions with its corresponding mass-to-charge ratio. As a result, it becomes possible to recognize partial pressures of the each gas in the vacuum apparatus and the like are made recognizable.

Note that the control, the operation, the display of various pieces of information, and the like performed by the controlling PC 62 may be performed by the electric system portion 14.

Figure 2:
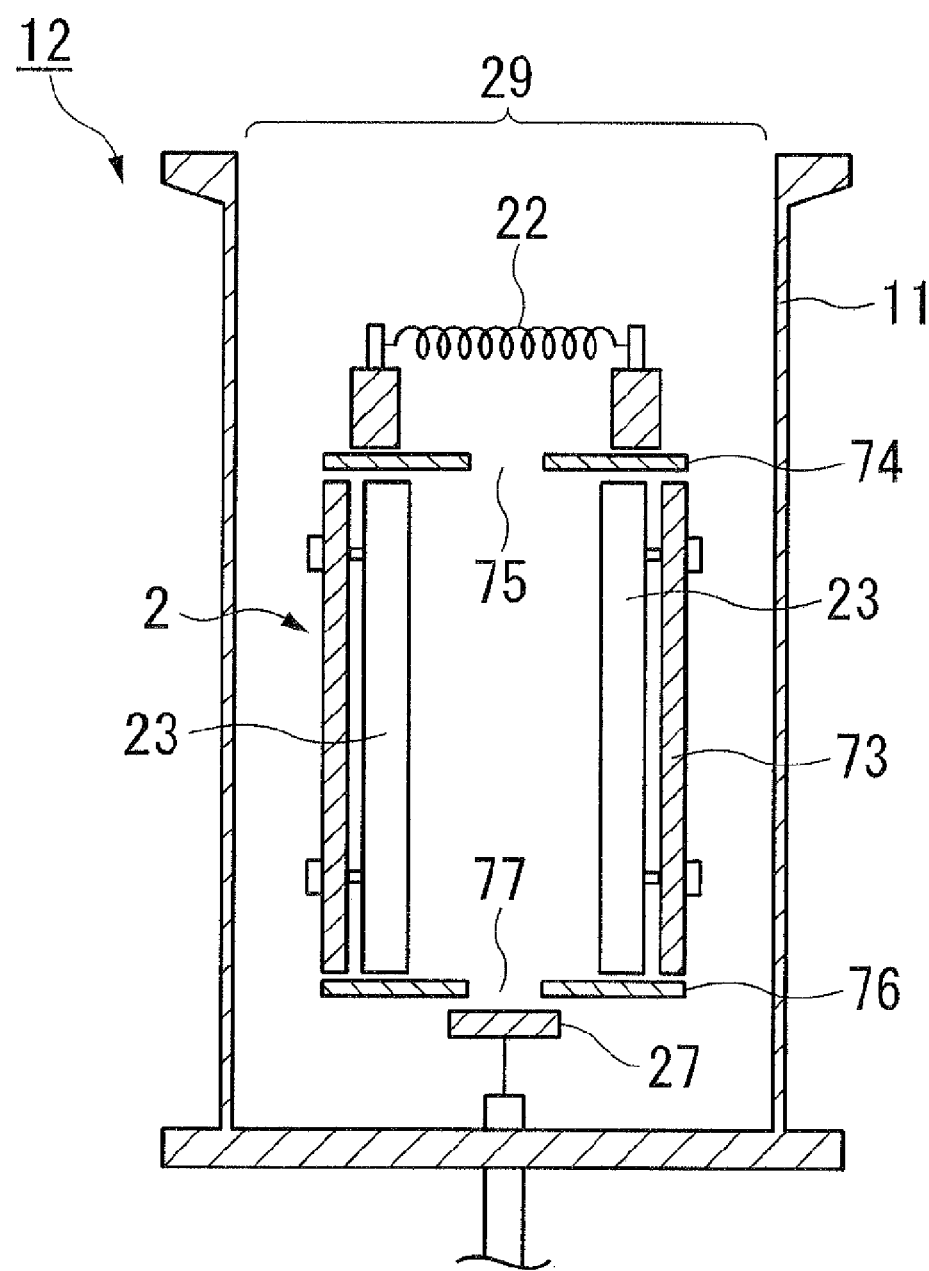
FIG. 2 is a cross-sectional view showing an internal construction of a measurement portion according to the embodiment.

FIG. 2 is a diagram showing an internal construction of the measurement portion 12.

As shown in FIG. 2, the measurement portion 12 has a metal-made container 11 with a bottom. The container 11 has a shape of a cylinder hollow with one end open. There is arranged a mass selection portion 2 therein. An opening 29 side is connected to a vacuum apparatus (described later).

First, the mass selection portion 2 will be described. The mass selection portion 2 has: an attachment barrel 73; an ion source portion 22; a quadrupole 23; and an ion detection portion 27.

The attachment barrel 73 is formed of an insulating material shaped into a cylinder hollow. Of its two openings, one is directed toward the opening 29 of the container 11, and the other is directed toward the ion detection portion 27.

The quadrupole 23 is made of four electrodes, each formed of a metal-made cylinder. The quadrupole 23 is arranged in the interior of the attachment barrel 73 (in FIG. 2, two of the electrodes are seen). The four poles constituting the quadrupole 23 are each directed in the direction along the central axis line of the attachment barrel 73. They are fixedly threaded on the wall surface of the interior of the attachment barrel 73 with a predetermined distance spaced apart from each other.

The ion source portion 22 is a thermal filament. As the ion source portion 22, for example one in which a yttrium oxide is coated on an iridium (Ir) wire is used. The ion source portion 22 is arranged at a position near an opening of the attachment barrel 73, between the opening and the opening 29 of the container 11. Furthermore, between the ion source portion 22 and the quadrupole 23, there is arranged a slit 74.

A gas present in the vacuum apparatus to be measured travels into the container 11 through the opening 29 of the container 11. Therefore, the atmosphere in the container 11 is the same as that in the vacuum apparatus. Consequently the atmosphere around the ion source portion 22 has the same composition as that inside the vacuum apparatus.

When the ion source portion 22 is energized to cause the ion source portion 22 to emit thermions, the thermions collide with the gas molecules around the ion source portion 22, to thereby generate ions.

The slit 74 has a small hole 75. The small hole 75 is positioned between the four electrodes constituting the quadrupole 23. The ions generated by the ion source portion 22 pass through the small hole 75 of the slit 74 into the quadrupole 23.

To each of the electrodes constituting the quadrupole 23, there is applied a voltage in which an alternating-current voltage at a predetermined frequency is superimposed on a direct-current bias voltage. Of the ions having traveled into the quadrupole 23, only those with a mass-to-charge ratio in accordance with the size of the direct-current bias voltage and the size of the alternating-current voltage pass through the quadrupole 23. Therefore, a change in the sizes allows only ions with a desired mass-to-charge ratio to pass.

There is arranged a slit 76 between the attachment barrel 73 and the ion detection portion 27.

Therefore, the ions having passed through the quadrupole 23 fly toward a small hole 77 of the slit 76, pass through the small hole 77, and then are incident on the ion detection portion 27.

When the ions are incident on the ion detection portion 27, an ion current is detected. As the ion detection portion 27, a secondary electron multiplier tube made of a Cu—Be alloy, an aluminum oxide (AlO), or the like, or a Faraday cup made of stainless steel (SUS) or the like may be used. In the present embodiment, a secondary electron multiplier tube is used as the ion detection portion 27. A secondary electron multiplier tube causes ions to collide with a metal surface of the secondary electron multiplier tube at high speed, to thereby generate secondary electrons. This amplifies one ion several-fold. Therefore, it is possible to improve the sensitivity in detection.

(Usage of Mass Spectrometry Unit)

Figure 3:
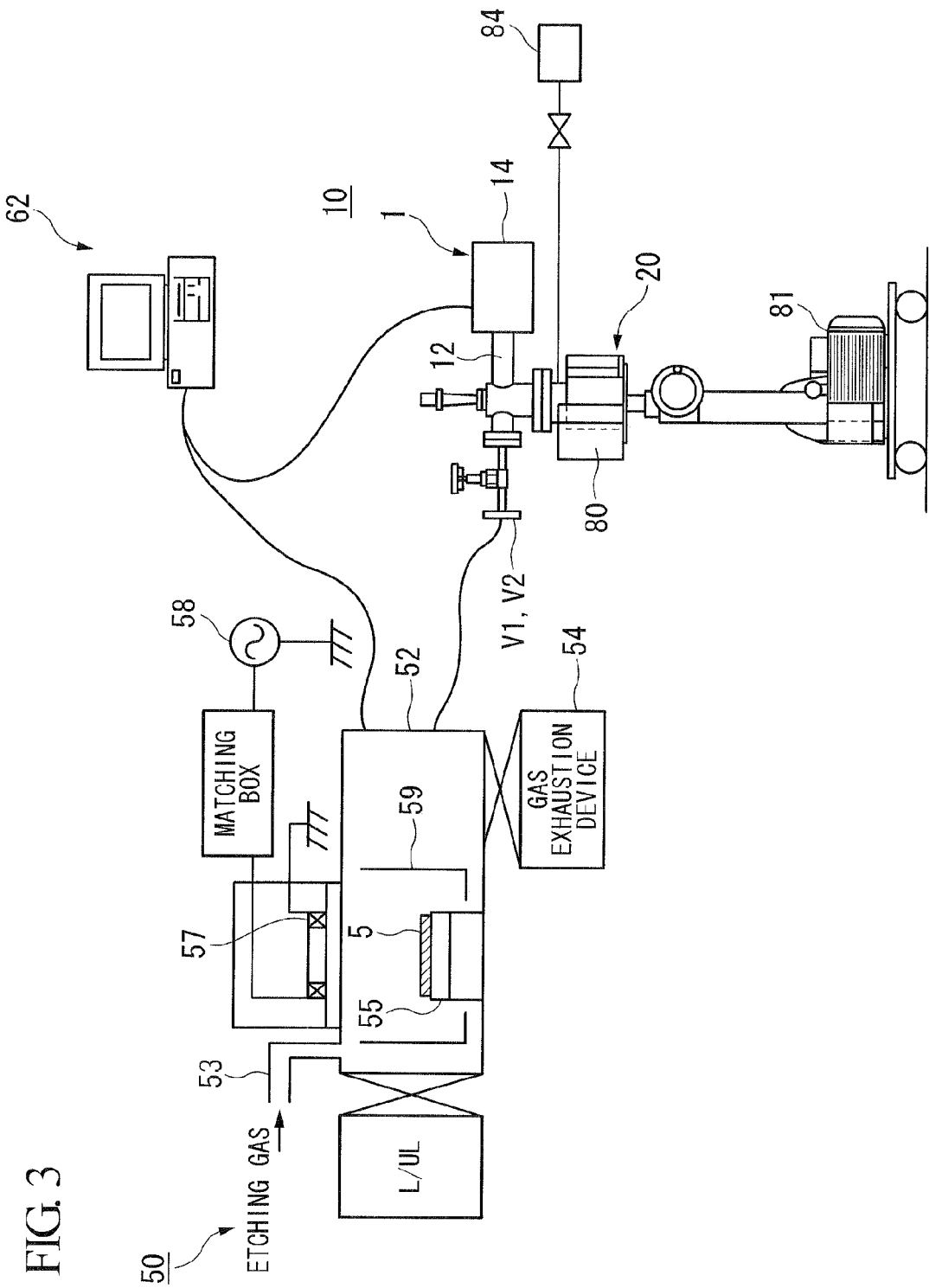
FIG. 3 is a schematic block diagram showing an etching apparatus attached with the mass spectrometry unit according to the embodiment.

Next is a description of usage of the mass spectrometry unit 10 according to the present embodiment based on FIG. 3.

FIG. 3 is a schematic block diagram showing a vacuum apparatus attached with the mass spectrometry unit 10 according to the present embodiment.

As a vacuum apparatus to which the mass spectrometry unit 10 is attached, a reactive ion etching (RIE) apparatus 50 with the inductive coupling plasma (ICP) system will be described below by way of example. The reactive ion etching apparatus 50 (hereinafter, referred to as an "etching apparatus 50") includes an airtightly-sealed chamber 52. To the chamber 52, there are connected a gas supply device 53 for an etching gas and a gas exhaustion device 54 for a gas in the chamber 52. In the chamber 52, there is provided a stage 55 on which a substrate 5 is mounted. To prevent an etching product from depositing on the inner wall of the chamber 52, there is provided a deposition preventing plate 59 so as to surround the stage 55.

On the other hand, to generate a plasma in the chamber 52, an antenna 57 is arranged above the chamber 52. The antenna 57 is connected to a plasma high-frequency power source 58.

To perform etching in the etching apparatus 50 with such a construction, firstly the substrate 5 is mounted on the stage 55, and the substrate 5 is maintained at a predetermined temperature. Next, an etching gas is supplied from the gas supply device 53, to thereby maintain the chamber 52 at a predetermined pressure. Next, The plasma high-frequency power source 58 is driven to apply a high-frequency voltage to the antenna 57. As a result, a plasma is generated in the chamber 52, and the etching gas is excited. Consequently, active species such as ions and radicals are generated. The radicals generated here act on the substrate 5, to generate volatile substances including an etching substance. Thus, an etching treatment is performed.

The etching apparatus 50 is connected to the controlling PC 62 that is spaced from the chamber 52. The operation of the etching apparatus 50 can be controlled by the controlling PC 62. That is, the controlling PC 62 is connected to both of the mass spectrometry unit 10 and the etching apparatus 50. Therefore, the controlling PC 62 is capable of controlling the mass spectrometry unit 10 and the etching apparatus 50.

As the above etching gas, a corrosive/halogen-based gas such as hydrofluoric acid (HF) or chlorine (Cl) is used.

A gas supply tube provided in the side wall of the chamber 52 is connected to the selector valves V1, V2 that constitute the gas introduction portion 24 in the mass spectrometry unit 10. It is configured such that a gas to be measured is introduced into the measurement portion 12 via the gas introduction portion 24.

The principle of a mass analysis of the present embodiment is followings. The differential exhaustion portion 20 is used to introduce a gas to be measured (a specific gas) into the measurement portion 12 of the mass spectrometry portion 1. Next, the introduced gas molecules are ionized with the thermions generated by the thermal filament of the ion source portion 22. Next, an electric field by a direct-current voltage and an alternating current voltage is applied to the four rods of the quadrupole 23. Thereby, of the ions incident from the ion source portion 22, only ions with a specific mass-to-charge ratio are allowed to pass. Next, in the ion detection portion 27, the ions having passed through the quadrupole 23 are detected as an ion current. The electric field applied to the quadrupole 23 is swept to measure ion currents according to the mass-to-charge ratio, and to identify the types of gases and their partial pressure.

Figure 4:
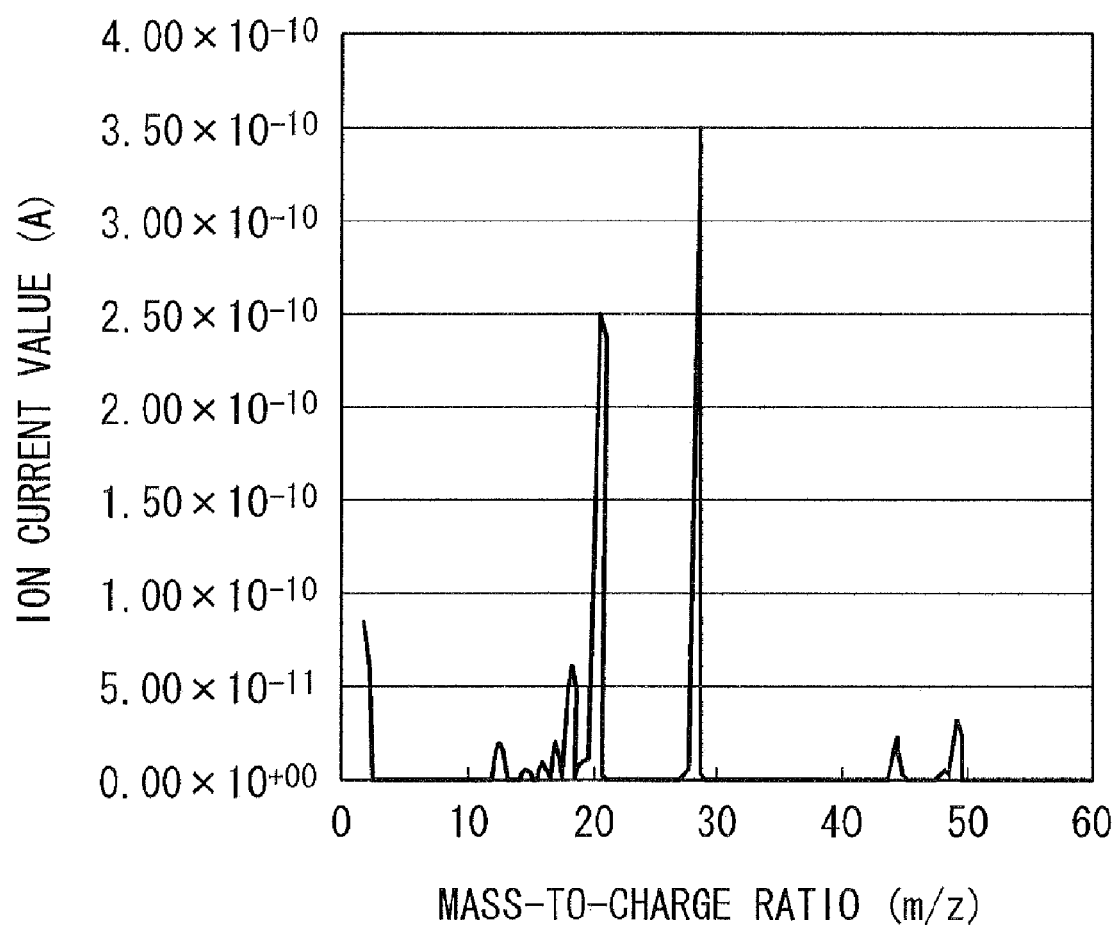
FIG. 4 is a graph showing a mass spectrum plotting of the mass-to-charge ratio vs. the ion current value.

Here, FIG. 4 is a graph showing a mass spectrum plotting of the ion current value (A) vs. the mass-to-charge ratio (m/z) in the case where a hydrofluoric acid (HF) is introduce into the chamber 52 as an etching gas.

A hydrofluoric acid has a mass-to-charge ratio of m/z=20. Therefore, a peak ($2.50 \times 10^{-10}$ (A)) occurs at m/z=20, as shown in FIG. 4. As a result, it can be determined that a hydrofluoric acid (HF) is introduced into the chamber 52.

Figure 5:
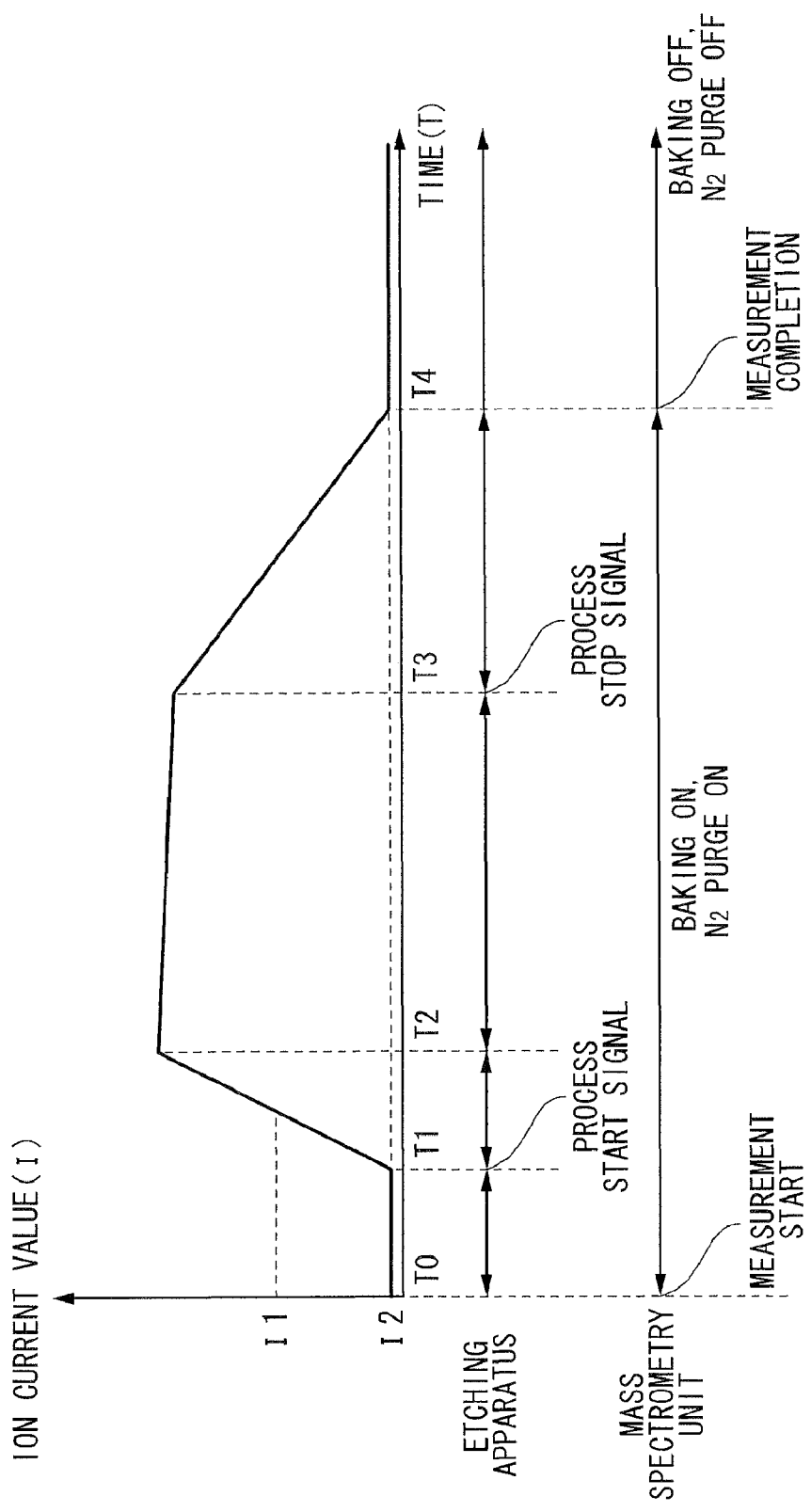
FIG. 5 is a graph showing a relationship between time and ion current value of a specific gas in an etching process, with corresponding operations of the etching apparatus and the mass spectrometry unit.

Here, FIG. 5 is a diagram showing a relationship between time (T) and the change in the ion current value (I) of a specific gas, with corresponding operations of the etching apparatus and the mass spectrometry unit.

As shown in FIG. 5, when the mass spectrometry unit 10 is operated at time T0, operation start signals for baking heaters 82a, 82b, 82c and the dilution gas supply portion 84 are output from the control portion 63. This starts the heating of the measurement portion 12 and the pumps 80, 81, and also the purge of the pumps 80, 81.

At the time when the measurement portion 12 and the pumps 80, 81 are sufficiently heated, (time T1), the measurement portion 12 is used to start a measurement of partial pressures according to the mass-to-charge ratio in the chamber 52 based on a process start signal. Then, based on the process start signal, an etching gas is introduced into the chamber 52 to perform an etching. After completion of the etching, the introduction of the etching gas is stopped based on a process stop signal (time T3). After the introduction of the etching gas is stopped, the remaining etching gas gradually decreases. Then, at time T4, the ion current value returns to the state before the introduction of the etching gas. Here, the state before the introduction of the etching gas (the period from T0 to T1, and after T4) is referred to as a background state.

(Preventive Maintenance Method)

Figure 6:
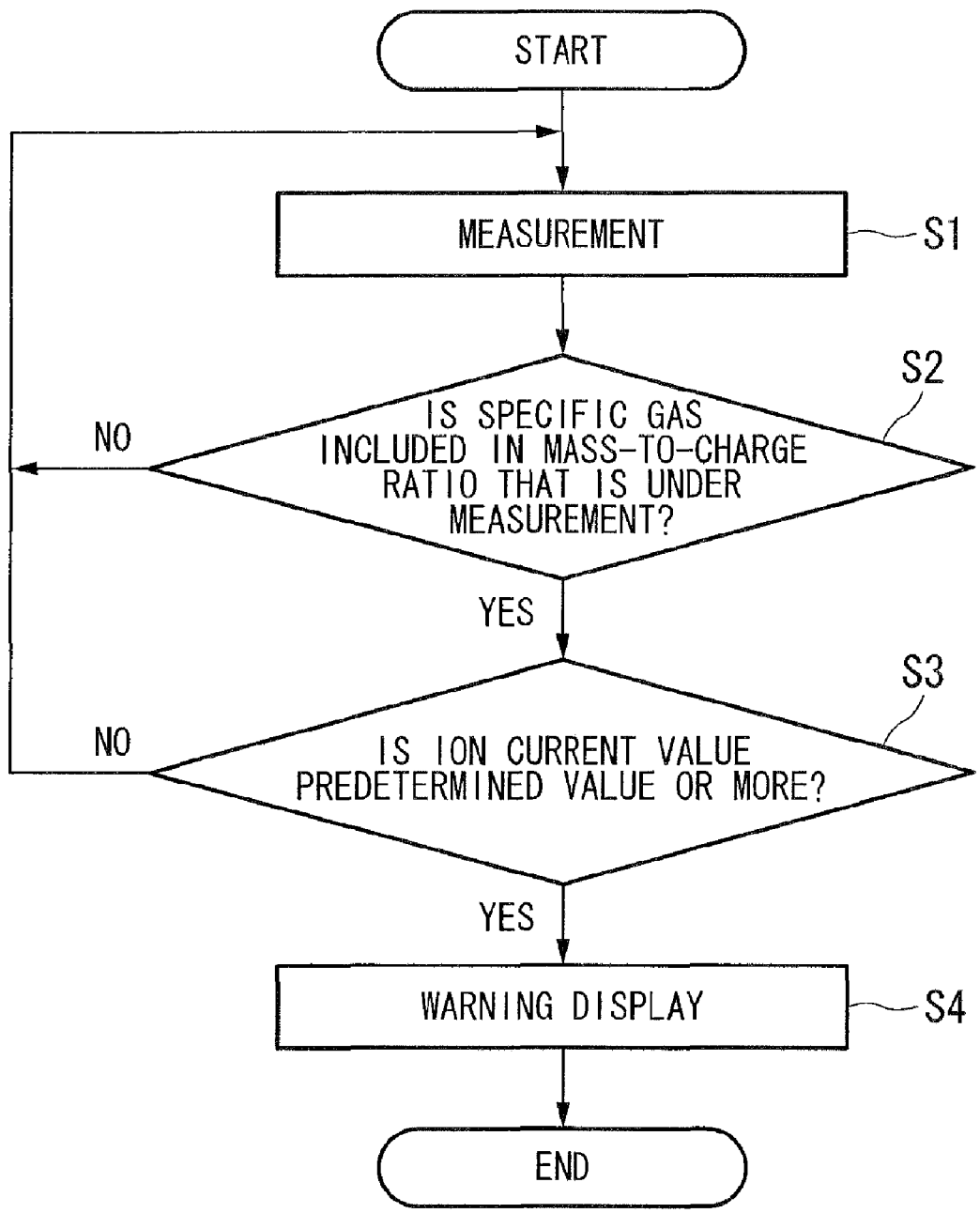
FIG. 6 is a flow chart showing a preventive maintenance method of the mass spectrometry unit according to the embodiment.

Hereunder is a description of a preventive maintenance method in the case where the etching apparatus 50 is attached with the mass spectrometry unit 10, based on FIG. 6 and Table 1. FIG. 6 is a flow chart showing the preventive maintenance method in the present embodiment. Note that the present preventive maintenance method will be described for the case where a hydrofluoric acid is introduced into the chamber 52 of the etching apparatus 50 as an etching gas (a specific gas).

When the ion source portion 22 in the mass spectrometry unit 10 is exposed to a corrosive/halogen-based gas such as a hydrofluoric acid, the coating on the surface of the ion source portion 22 made of a yttrium oxide comes off. This finally leads to a possibility of the occurrence of an anomaly such as a disconnection in the ion source portion 22 or stopping of an emission current flowing between the ion source portion 22 and the grid. Furthermore, the secondary electron multiplier tube used as the ion detection portion 27 is made of a Cu—Be alloy, an aluminum oxide (AlO), or the like. Therefore, if such a metal is exposed to chlorine or the like, there is a possibility that the metal is melted and deteriorated. Note that a gas that decreases the function of the specific portion (the ion source portion 22, the ion detection portion 27, or the like) in the mass spectrometry unit, like the aforementioned corrosive/halogen-based gas, will be hereinafter referred to as a "specific gas."

On the other hand, few users realize that specific gases facilitate a disconnection in the ion source portion 22 or the deterioration of the ion detection portion 27 and the like. In addition, few users realize when the peak of the mass-to-charge ratio for the introduced specific gas occurs. Therefore, many users are not aware that a specific gas has been introduced.

Furthermore, an unexpected specific gas may be introduced into the mass spectrometry unit 10. That is, such a specific gas may be introduced into a mass spectrometry unit 10 (for example, for a sputtering/vapor deposition apparatus) with low resistance to the specific gas. Continued introduction of the specific gas may lead to earlier deterioration of the ion source portion 22 and the ion detection portion 27.

Under the circumstances, the present inventors have found that it is possible to prevent a disconnection in the ion source portion 22 and a deterioration of the ion detection portion 27 by giving a warning to the user if, with the mass-to-charge ratios of specific gases being preset in the memory portion 64, an ion current value of a detected specific gas is not less than a corresponding predetermined value.

To be more specific, at first, predetermined values of mass-to-charge ratios and ion current values of specific gases are set.

Table 1 shown below is a correspondence table between specific gases that are introduced into the etching apparatus 50 to decrease the functions of the ion source portion 22, the ion detection portion 27, and the like (for example, corrosive/halogen-based specific gases in the case where the mass spectrometry unit 10 is attached to the etching apparatus) and mass-to-charge ratios of the respective specific gases.

TABLE 1

| Mass-to-charge ratio (m/z) | Gas species |
|---|---|
| 20 | HF |
| 35 | Cl |
| 70 | $Cl_2$ |
| 71 | $NF_3$ |
| 81 | HBr |
| 88 | $CF_4$ |
| 100 | $SiH_2Cl_2$ |
| 138 | $C_2F_6$ |

A correspondence table for the mass-to-charge ratios of the specific gases is preset as shown in Table 1. This data is recorded in the memory portion 64. Then, a predetermined value of the ion current value for the mass-to-charge ratio corresponding to each specific gas in Table 1 is set for every specific gas, and is recorded in the memory portion 64.

It is preferable that the predetermined values in the present preventive maintenance method be set to values not less than the corresponding ion current values detected in the aforementioned background state (for example, I1 in FIG. 5). As a result, it is possible to detect the introduction of a specific gas at an early stage.

When a gas to be measured (a specific gas) is ionized, a peak called a cracking pattern appears due to the dissolution of the gas molecules. In FIG. 4, a peak occurs at m/z=20 also before the introduction of the hydrofluoric acid. Therefore, it is preferable that the predetermined value be not less than the ion current value of a peak that can be produced by a cracking pattern. As a result, a peak by a specific gas is discriminated from a peak by a cracking pattern, to thereby make it possible to prevent an erroneous operation of the mass spectrometry unit 10, and hence to secure the reliability of the mass spectrometry unit 10.

Next, as shown in FIG. 6, the measurement portion 12 is used to start a measurement of partial pressures according to the mass-to-charge ratio in the chamber 52 (step S1). As for the measurement method, the electric field applied to the quadrupole 23 is swept to measure the ion currents according to the mass-to-charge ratio, and to identify the types of gases and their partial pressure, as described above.

Table 1 is checked for the mass-to-charge ratio under measurement to determine a specific gas of a preset mass-to-charge ratio (for example, m/z=20) is present or not (step S2). Here, if a peak of an ion current value is not detected, and hence no specific gas is included (if the determination in step S2 is No), then a signal for continuing the measurement is output from the control portion 63 to the electric system portion 14, to thereby continue a measurement of another mass-to-charge ratio. On the other hand, if a peak of an ion current value is detected (if the determination in step S2 is Yes), then it is determined whether or not the ion current value at the peak is more than the corresponding predetermined value that is set in the memory portion 64 (step S3).

If the ion current value at the peak is less than the predetermined value (if the determination in step S3 is No), then measurement by the measurement portion 12 is continued. On the other hand, if the ion current value at the peak is not less than the predetermined value (if the determination in step S3 is Yes), then it is determined that a specific gas is introduced. In this case, a warning signal is output from the control portion 63 to the display portion 65. As for this warning signal, a warning signal is output in accordance with possible causes of the functional decrease in a specific portion such as a possibility of a disconnection in the ion source portion 22, an anomaly in an emission current value, a deterioration of the ion detection portion 27, and the like.

On receiving the warning signal, the display portion 65 lights up the information denoting a warning display based on the signal (step S4). This promptly notifies the user where in the ion source portion 22 and the ion detection portion 27 there is a possibility of a functional decrease. Note that the warning display may be configured to be recognizable by means not only of visible information on the display portion 65 but also of sound provided by a buzzer or the like.

After displaying the warning, the control portion 63 outputs a signal for continuing a measurement to the electric system portion 14 to continue a measurement of another mass-to-charge ratio. Thus, the control portion 63 continues the measurement to check whether the other specific gases (the specific gases other than the hydrofluoric acid shown in Table 1) is introduced or not in the similar manner to the above flow.

Therefore, in the preventive maintenance method for the mass spectrometry unit 10 in the present embodiment, mass-to-charge ratios of specific gases that decrease the function of the ion source portion 22, of the ion detection portion 27, and of the like are previously recorded in the memory portion 64; and if an ion current value of any of the specific gases is not less than the corresponding predetermined value, then the control portion 63 outputs a warning signal to the display portion 65.

With this configuration, if an ion current value of any of the specific gases exceeds the corresponding predetermined value, then the control portion 63 outputs a warning signal. Thereby, even a user unaware of the mass-to-charge ratios of the specific gases can be promptly notified of the possibility of a disconnection in ion source portion 22 in the mass spectrometry unit 10 or of a deterioration of the ion detection portion 27. Therefore, it is possible to prevent a break in the ion source portion 22 and deterioration of the ion detection portion 27 due to the specific gases. Consequently, it is possible to efficiently use the ion source portion 22 and the ion detection portion 27 for a long period of time.

Furthermore, if the preventive maintenance method of the present embodiment is used for a mass spectrometry unit with low resistance to a specific gas, it is possible to promptly notify the user of the possibility of a functional decrease in the mass spectrometry unit even in the case where the mass spectrometry unit with low resistance to the specific gases is attached to an etching apparatus due to failure in observance of instructions and directions for use.

Second Embodiment (Operating Life Management Method)

Figure 7:
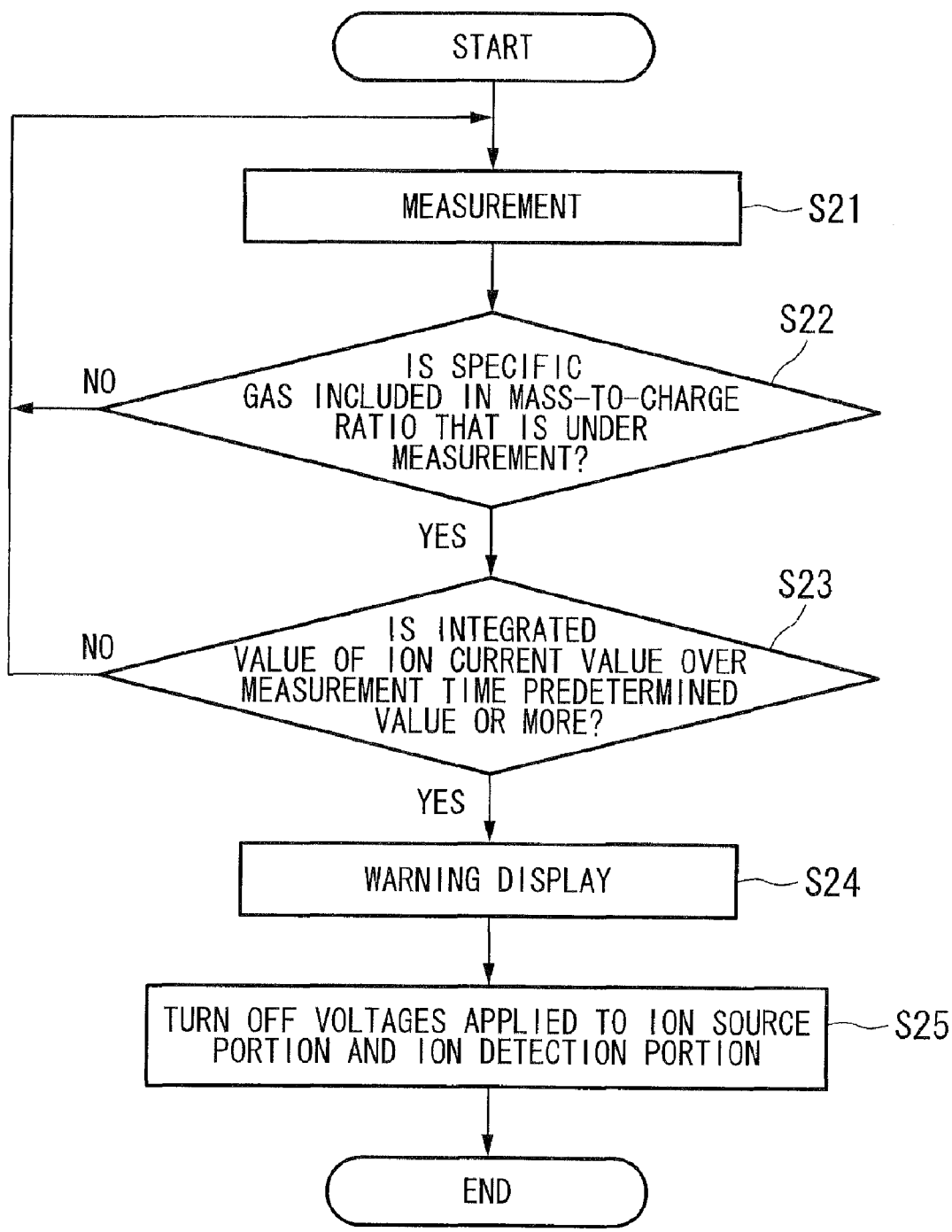
FIG. 7 is a flow chart showing a preventive maintenance method of the mass spectrometry unit according to the embodiment.

Next is a description of a second embodiment of the present invention based on a flow chart of FIG. 7. The present embodiment is an operating life management method in the case where the mass spectrometry unit 10 is attached to the etching apparatus 50. It is different from the above first embodiment in that a predetermined value is set based on an integrated value of an ion current value over a detection time.

It is obvious that the higher the peak of the ion current value for the mass-to-charge ratio that is set for a specific gas in the memory portion 64 is, the larger the amount of the specific gas introduced into the chamber 52 of the etching apparatus 50 is. With the larger amount, the operating life of parts such as the ion source portion 22, the ion detection portion 27, and the like (hereinafter, referred to as expendable parts) becomes shorter. Furthermore, the longer the time during which a specific gas is being detected is, the shorter the operating life of expendable parts is. The continued measurement with expendable parts whose operating life is over brings about an incorrect result. Therefore, it is necessary to replace the expendable parts regularly. The time for their replacement is subject to change according to kind of the specific gas, the use situation and status of use.

Therefore, as for these expendable parts, it is difficult to determine the correct time for their replacement. For example, if expendable parts are replaced after they are unusable and a correct measurement is impossible, it takes a long time to replace the expendable parts. Then, there arises a problem of an extended period in which use of the mass spectrometry unit 10 is suspended. In addition, if the expendable parts are replaced in advance even though they are still usable, then the efficiency of the expendable parts is poor. Then, there arises problems such as losses of resources and increased costs.

Under the circumstances, the present inventors have found that it is possible to solve the aforementioned problems by an operating life management method for an expendable part in which an integrated value of an ion current value of a detected specific gas over a detection time is found; and if the integrated value exceeds a preset predetermined value, then a warning is given to the user and also an application of voltages to the ion source portion 22 and the ion detection portion 27 is cancelled.

To be more specific, at first, mass-to-charge ratios of specific gases are set, and also a predetermined value for every specific gas is set. The mass-to-charge ratios and the predetermined values are recorded in the memory portion 64 in advance. In the predetermined values in the present operating life management method, it is preferable that the integrated value of the ion current value of the detected specific gas over the detection time be not greater than the integrated value of the ion current value over the time till the expendable parts reach the end of their operating life.

Next, as shown in FIG. 7, a measurement is started similarly to steps S1, S2 in the aforementioned preventive maintenance method, to thereby determine whether a specific gas with a specific mass-to-charge ratio is present or not (steps S21, S22).

Here, if a peak of an ion current value is not detected, and hence no specific gas is included (if the determination in step S22 is No), then a signal for continuing the measurement is output from the control portion 63 to the electric system portion 14, to thereby cause the measurement portion 12 to continue a measurement of another mass-to-charge ratio. On the other hand, if a peak of an ion current value is detected (if the determination in step S22 is Yes), then an integrated value of the ion current value at the peak over a detection time is calculated and recorded in the memory portion 64. Note that a detection time is a period during which a specific gas is determined to be present by this measurement. If the integrated value until the former measurement is already recorded, the integrated value in this measurement is added to the former integrated value, and the resultant integrated value is recorded. Then, it is determined whether the integrated value currently recorded is not less than the corresponding predetermined value set in the memory portion 64 (step S23).

If the integrated value is less than the corresponding predetermined value (if the determination in step S23 is No), the measurement by the measurement portion 12 is continued. On the other hand, if the integrated value is not less than the corresponding predetermined value (if the determination in step S23 is Yes), it is determined that the expendable parts are coming close to the end of their operating life. In this case, similarly to the aforementioned step S4, a warning signal is output from the control portion 63 to the display portion 65. As for this warning signal, a warning signal is output in accordance with the expendable part requiring replacement due to a possible disconnection in the ion source portion 22, an anomaly in an emission current value, a deterioration of the ion detection portion 27, and the like. On receiving the warning signal, the display portion 65 lights up the information denoting a warning display based on the signal (step S24). As a result, the user can determine when to replace the expendable part.

Here, at the same time of the warning display on the display portion 65, the control portion 63 outputs to the electric system portion 14 a stop signal for canceling the application of the voltages to the ion source portion 22 and the ion detection portion 27 (step S25). On receiving the signal, the electric system portion 14 cancels the application of the voltages to the ion source portion 22 and the ion detection portion 27, to thereby stop the measurement. As a result, it is possible to suppress further deterioration of the expendable parts.

Therefore, in the operating life management method for the mass spectrometry unit 10 in the present embodiment, if an integrated value of an ion current value of any of the specific gases over a detection time during which the ion current value is being detected is not less than the corresponding predetermined value, a warning signal is output. And also in this case, an application of voltages to the ion source portion 22 and the ion detection portion 27 is canceled, to thereby stop the measurement.

With this configuration, if the integrated value of the ion current value of the specific gas over the detection time during which the ion current value is being detected is not less than the corresponding predetermined value, a warning is displayed on the display portion 65. Thereby, it is possible to correctly notify a change over time of expendable parts such as the ion source portion 22 and the ion detection portion 27. Furthermore, the application of voltages to the expendable parts is canceled to stop the measurement. Thereby, it is possible to suppress a further change over time of the expendable parts.

Furthermore, in the present embodiment, the predetermined value is set to not less than the integrated value over the operating life of the ion source portion 22 and the ion detection portion 27.

With this configuration, the predetermined value is set to not less than the integrated value over the operating life of the ion source portion 22 and the ion detection portion 27, to thereby make it possible to correctly notify an operating life of expendable parts such as the ion source portion 22 and the ion detection portion 27. That is, although the time for replacement of the expendable parts such as the ion source portion 22 and the ion detection portion 27 is subject to change according to the condition of use and the circumstances of use of the mass spectrometry unit 10, it is possible for the user to determine the time for their replacement according to the warning display. Consequently, it is possible to shorten the period in which use of the mass spectrometry unit 10 is suspended after the expendable parts become unusable. This can improve operating efficiency. Furthermore, it is possible to prevent advance replacement of the ion source portion 22 and the ion detection portion 27 while they are still usable. Therefore, it is possible to improve use efficiency of the ion source portion 22 and the ion detection portion 27, and to achieve lower costs and resource saving.

Third Embodiment (Parts Management Method)

Next is a description of a third embodiment of the present invention based on FIG. 8. The present embodiment is a parts management method in the case where the mass spectrometry unit 10 is attached to the etching apparatus 50. FIG. 8 is an exemplary record of serial numbers of the measurement portion and the pumps 80, 81, and specific gases.

The aforementioned expendable parts such as the ion source portion 22 and the ion detection portion 27 are parts with an operating life, and hence inevitably require replacement. In addition, the pumps 80, 81 of the differential exhaustion portion 20 require regular overhaul (hereinafter, regular overhaul work or replacement work of an expendable part will be referred to as "repair work," and a part that requires overhaul or an expendable part that requires replacement will be referred to as a "part to be repaired."). Incidentally, repair work of a part to be repaired is typically performed by a worker other than the user. In this case, there is a possibility that a specific gas or the like is deposited on the part to be repaired. Therefore, the worker should check whether there is a deposition of a specific gas or not to secure the safety of the work.

Therefore, in the conventional repair work of the part to be repaired, the worker asks the user for an introduction history of specific gases in advance, and then begins the work. This results in a problem of poor operational efficiency.

Under the circumstances, the present inventors have found that it is possible to solve the above problem in the following manner. Mass-to-charge ratios of the specific gases that require a check for the presence of their deposition are previously recorded in the memory portion 64. Then, when a specific gas is introduced, information on the specific gas and information on the part to be repaired are recorded.

To be more specific, a measurement is performed similarly to the steps up to step S2 in the aforementioned preventive maintenance method (see FIG. 6).

Then, if a peak of an ion current value is not detected, and hence no specific gas is included, then a signal for continuing the measurement is output from the control portion 63 to the electric system portion 14, to thereby continue a measurement of another mass-to-charge ratio. On the other hand, if a peak of an ion current value is detected, an integrated value of the ion current value over a detection time is recorded in the memory portion 64. If the integrated value until the former measurements is already recorded, the integrated value in this measurement is added to the former integrated value, and the resultant integrated value is recorded. To be more specific, as shown in FIG. 8, data of an integrated value of each ion current value of each detected specific gas over the detection time is recorded in the memory portion 64, in correspondence to the mass-to-charge ratio of each specific gas.

Concurrently with the recording of the data of the integrated value in the memory portion 64, the serial number of the measurement portion 12 in use at that time (for example, Analysis Tube Serial Number in FIG. 8) and the serial number of the pumps 80, 81 (for example, Pump Serial Number in FIG. 8) are recorded in the memory portion 64. These records are stored in a server from the control portion 63 via a network. When the worker reads out this information in the repair work of a part to be repaired, information as shown in FIG. 8 is displayed on the display portion 65.

Therefore, in the parts management method of the mass spectrometry unit 10 in the present embodiment, if an ion current value of a mass-to-charge ratio of a specific gas is detected by the measurement portion 12, then an integrated value of the ion current value of the specific gas over the detection time during which the ion current value is being detected is recorded, and also information on a part to be repaired such as the measurement portion 12, the differential exhaustion portion 20 and the like is recorded.

With this configuration, when the expendable parts such as the ion source portion 22, the ion detection portion 27 and the like are replaced or when the pumps 80, 81 are overhauled, the information recoded in the memory portion 64 is read out. Thereby, it is possible to check the introduction history of the specific gases correctly and speedily. Therefore, even when a worker other than the user performs replacement or overhaul work, the worker is allowed to do their work with efficiency and with their safety secured.

Fourth Embodiment (Power Saving Method)

Figure 9:
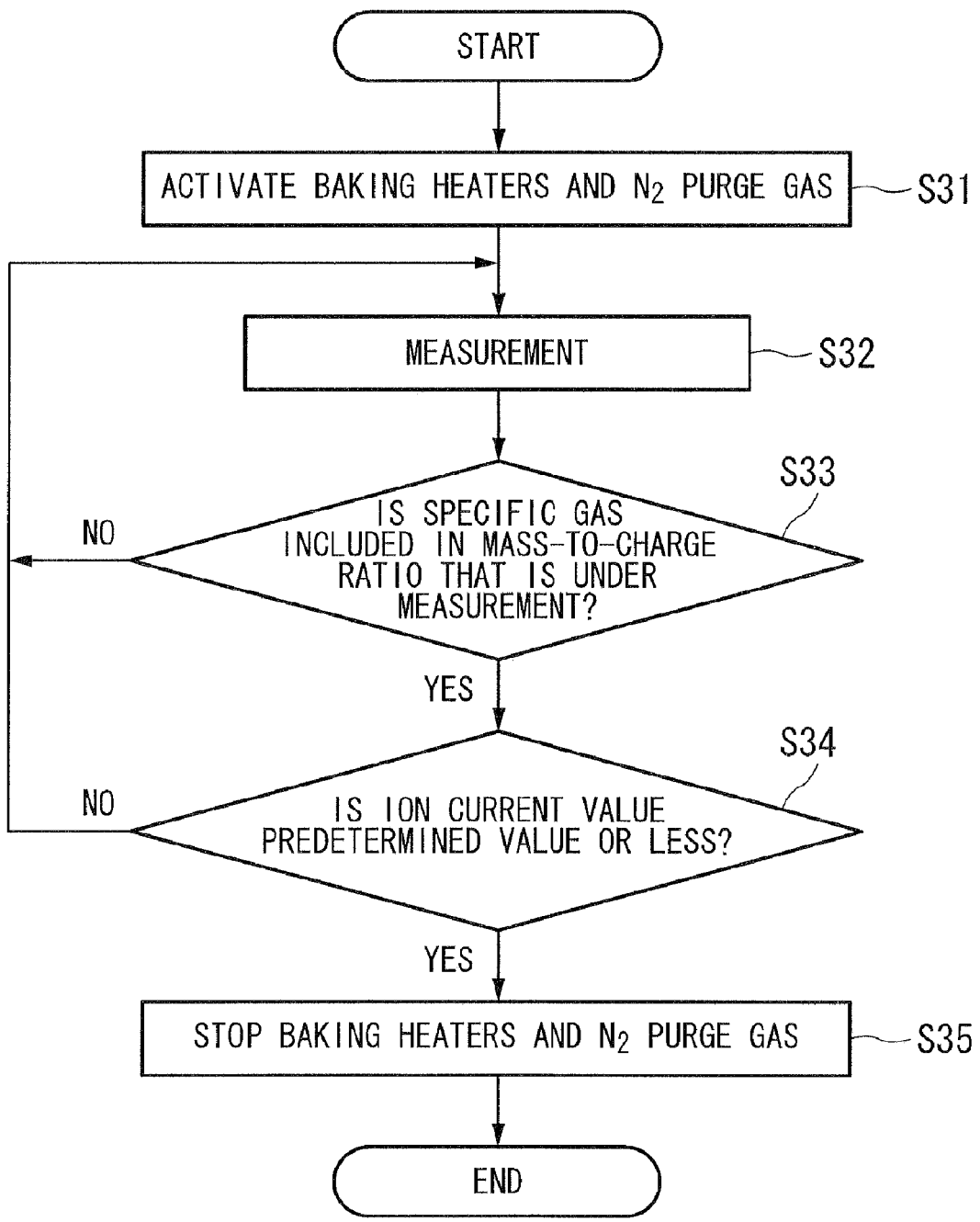
FIG. 9 is a flow chart showing a power saving method of the mass spectrometry unit of the embodiment.

Next is a description of a fourth embodiment of the present invention based on a flow chart of FIG. 9. The present embodiment is a power saving method of the mass spectrometry unit 10 after completion of the etching process (after time T3 in FIG. 5).

As described above, during the introduction of a specific gas, the baking heaters 82a, 82b, 82c are used to heat the measurement portion 12 and the pumps 80, 81. At the same time of the specific gas introduction, the dilution gas supply portion 84 is used to flow a purge gas in order to dilute the specific gas flowing through the pumps 80, 81. However, if a specific gas is not introduced after, for example, completion of the etching process or the like, it is not necessary to heat the measurement portion 12 and the pumps 80, 81, and to purge the pumps 80, 81.

Nevertheless, if the operation of the heating of the measurement portion 12 and the pumps 80, 81, and the operation of the $N_2$ purge of the pumps 80, 81 are continued, there arises a problem of wasting electric power and of purge gas.

Under the circumstances, the present inventors have found that it is possible to save power by stopping the heating of the measurement portion 12 and the pumps 80, 81, and the $N_2$ purge of the pumps 80, 81 at the time when, after completion of the etching process, the ion current value of the specific gas goes below a predetermined value, and hence there is no adverse effect on the pumps 80, 81.

To be more specific, at first, mass-to-charge ratios of specific gases are set and predetermined values of ion current values are set. It is preferable that the predetermined values are set in the vicinity of the ion current value in the aforementioned background state (I2 in FIG. 5).

Then, as shown in FIG. 9, the baking heaters 82a, 82b, 82c are activated to supply a purge gas from the dilution gas supply portion 84 to the pumps 80, 81 (step S31). It is preferable that this activation be started (T0 in FIG. 5) several hours before the process start signal (T1 in FIG. 5) because it takes time to heat the baking heaters 82a, 82b, 82c to bring the measurement portion 12 and the pumps 80, 81 to a predetermined temperature.

Then, based on the process start signal, a specific gas is introduced to start the etching. At the same time, the measurement portion 12 is used to start measuring partial pressures in the chamber 52 according to the mass-to-charge ratio. After that, based on the process stop signal, the introduction of the specific gas is stopped, which completes the etching process (T3 in FIG. 5).

Here, even after completion of the etching process, the measurement is continued in a similarly steps S1, S2 of the preventive maintenance method in the first embodiment (see FIG. 6), to thereby determine whether a specific gas with a preset mass-to-charge ratio is present or not (steps S32, S33).

If a peak of the ion current value is not detected, and hence no specific gas is included (if the determination in step S33 is No), then a signal for continuing the measurement is output from the control portion 63 to the electric system portion 14, to thereby cause measurement portion 12 to continue a measurement of another mass-to-charge ratio. On the other hand, if a peak of an ion current value is detected (if the determination in step S33 is Yes), a measurement is made to see whether or not the ion current value at the peak is not greater than the corresponding predetermined value that is set in the memory portion 64 (step S34).

If the ion current value at the peak is greater than the corresponding predetermined value (if the determination in step S34 is No), then the operation of heating by the baking heaters 82a, 82b, 82c and the operation of supplying the purge gas from the dilution gas supply portion 84 are continued, to thereby continue the measurement by the measurement portion 12. On the other hand, if the ion current value at the peak is not greater than the corresponding predetermined value (if the determination in step S34 is Yes), then it is determined that the ion current value is in the background state, and hence that no specific gas is introduced into the chamber 52. In this case, a stop signal is output from the control portion 63 to the electric system portion 14. On receiving the signal, the electric system portion 14 stops the heating by the baking heaters 82a, 82b, 82c and the supply of the purge gas from the dilution gas supply portion 84 (step S35). As described above, the measurement by the mass spectrometry unit 10 is completed.

Note that if the specific gas is re-introduced after the stop of the measurement, the step S31 and the subsequent steps are similarly followed with a process start signal for a restart regarded as the aforementioned process start signal Therefore, in the power saving method of the mass spectrometry unit 10 in the present embodiment, if the ion current value of the specific gas is not greater than the corresponding predetermined value, the heating by the baking heaters 82a, 82b, 82c of the differential exhaustion portion 20 and the supply of the purge gas from the dilution gas supply portion 84 are stopped.

With this configuration, at the time when the introduction of the specific gas is stopped and the possibility of an influence on the baking heaters 82a, 82b, 82c and the dilution gas supply portion 84 is eliminated, the heating by the baking heaters 82a, 82b, 82c of the differential exhaustion portion 20 and the supply of the purge gas from the dilution gas supply portion 84 are automatically stopped. Thereby, it is possible to achieve power saving of the mass spectrometry unit 10.

While exemplary embodiments of the invention have been described above with reference to the accompanying drawings, these are not to be considered as limitative of the invention. Obviously, combinations and the like of the constituent members illustrated above are merely examples, and various modifications based on design requirements and the like can be made without departing from the spirit or scope of the invention.

For example, in the preventive maintenance method according to the above first embodiment, a warning is displayed at the time when the ion current value is above the corresponding predetermined value. However, the corresponding predetermined value may be set based on the integrated value of the ion current value over the detection time, similarly to the above second embodiment.

Note that gases that can deteriorate the ion source portion 22 or the ion detection portion 27 include, for example, gases that are introduced into a CVD apparatus, such as tungsten hexafluoride ($WF_6$) for depositing a metal film and such as $SiH_2Cl_2$ and $NH_3$ for depositing an insulating film.

Influences of the above gases for depositing a metal film/insulating film on the ion source portion 22 and the ion detection portion 27 includes the followings. Deposition of a metal/insulating film on the ion detection portion 27, for which the secondary electron multiplier tube is used, makes it difficult to generate secondary electrons from its metal surface. Furthermore, deposition of a metal/insulating film on the ion source portion 22 results in a possibility of a cessation of an emission current and the like.

Therefore, as in the first to fourth embodiments of the present invention, the mass-to-charge ratios of gases for depositing a metal/insulating film is preset in the memory portion 64, and also a predetermined value of an ion current value of a gas for depositing a metal/insulating film with each mass-to-charge ratio is set. Thereby, it is similarly applicable to the gases for depositing a metal/insulating film. As a result, even if the mass spectrometry unit 10 is used for a CVD apparatus into which a gas for depositing a metal/insulating film is introduced, it is possible to achieve power saving and to efficiently use expendable parts such as the ion source portion 22 and the ion detection portion 27.

INDUSTRIAL APPLICABILITY

According to the present invention, it is possible to provide a mass spectrometry unit capable of preventing a functional decrease in a specific portion and capable of correctly grasping a deterioration time of the specific portion. Furthermore, according to the present invention, it is possible to provide a mass spectrometry unit capable of efficiently performing repair work of a part to be repaired or the like, and to achieve power saving.

What is claimed is:

1. A mass spectrometry unit including a mass spectrometry section that detects ion current values of a gas to be measured according to mass-to-charge ratio, to thereby measure partial pressures of the gas to be measured, the mass spectrometry unit further including:
a control section for preliminary storing a record of mass-to-charge ratios of specific gases that decrease a function of a specific section of the mass spectrometry unit, wherein
if an ion current value with the mass-to-charge ratio of any of the specific gases detected by the mass spectrometry section is not less than a corresponding predetermined value, the control section outputs a warning signal denoting a functional decrease in the specific section.

2. A mass spectrometry unit including a mass spectrometry section that detects ion current values of a gas to be measured according to mass-to-charge ratio, to thereby measure partial pressures of the gas to be measured, the mass spectrometry unit further including:

a control section for preliminary storing a record of mass-to-charge ratios of specific gases that decrease a function of a specific section of the mass spectrometry unit, wherein if an integrated value of an ion current value of any of the specific gases detected by the mass spectrometry section over a detection time during which the ion current value is being detected is not less than a corresponding predetermined value, the control section outputs a warning signal denoting a functional decrease in the specific section, and also cancels an application of a voltage to the specific section, to thereby stop a function of the specific section.

3. The mass spectrometry unit according to claim 2, wherein the predetermined value is not greater than an integrated value of the ion current value until a deterioration of the specific section over the detection time.

4. A mass spectrometry unit including a mass spectrometry section that detects ion current values of a gas to be measured according to mass-to-charge ratio, to thereby measure partial pressures of the gas to be measured, the mass spectrometry unit further including:

a control section for preliminary storing a record of mass-to-charge ratios of specific gases, the gases being checked for a presence or absence of a deposition thereof onto a part to be repaired at repair work of the mass spectrometry unit, wherein if an ion current value with the mass-to-charge ratio of any of the specific gases is detected by the mass spectrometry section, the control section records at least one of information on the specific gas and information on the part to be repaired.

5. A mass spectrometry unit including a mass spectrometry section that detects ion current values of a gas to be measured according to mass-to-charge ratio, to thereby measure partial pressures of the gas to be measured, the mass spectrometry unit further including:

a control section for preliminary storing a record of mass-to-charge ratios of specific gases that decrease a function of a specific section of the mass spectrometry unit; and a specific section maintenance device for preventing a functional decrease in the specific section due to any of the specific gases, wherein if an ion current value with the mass-to-charge ratio of any of the specific gases detected by the mass spectrometry section is not greater than a predetermined value, the control section stops the specific section maintenance device.

* * * * *